US00PP20868P2

(12) United States Plant Patent
Burton

(10) Patent No.: US PP20,868 P2
(45) Date of Patent: Mar. 23, 2010

(54) ***HEBE* PLANT NAMED 'SILVER LADY'**
(50) Latin Name: ***Hebe* hybrid**
Varietal Denomination: Silver Lady

(76) Inventor: Stephen Burton, 249 Peake Road, RD1 Cambridge (NZ)

( * ) Notice: Subject to any disclaimer, the term of this patent is extended or adjusted under 35 U.S.C. 154(b) by 0 days.

(21) Appl. No.: 12/322,731

(22) Filed: Feb. 6, 2009

(51) Int. Cl.
*A01H 5/00* (2006.01)

(52) U.S. Cl. ..... Plt./226
(58) Field of Classification Search ..... Plt./226
See application file for complete search history.

*Primary Examiner*—Annette H Para
(74) *Attorney, Agent, or Firm*—Penny J. Aguirre

(57) ABSTRACT

A new cultivar of *Hebe,* 'Silver Lady', characterized by its variegated foliage with olive-gray green centers and thin creamy white margins and its newly emerging leaves with a lower surface that is deep mauve-purple in color.

2 Drawing Sheets

Botanical classification: *Hebe* hybrid.
Cultivar designation: 'Silver Lady'.

BACKGROUND OF THE INVENTION

The present invention relates to a new and distinct cultivar of *Hebe,* botanically of hybrid origin and known as *Hebe* 'Silver Lady' and will be referred to hereafter by its cultivar name, 'Silver Lady'. 'Silver Lady' is grown for use as a container plant and as a landscape shrub.

The new cultivar was discovered as a branch mutation of the cultivar 'Orphan Annie' (non patented) in a container in the Inventor's nursery in September of 2005 in Cambridge, New Zealand.

Asexual reproduction of the new cultivar was first accomplished by the Inventor using terminal stem cuttings in Cambridge, New Zealand, in October 2005. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Silver Lady' as a new and distinct cultivar of *Hebe.*

1. 'Silver Lady' exhibits foliage in which the lower surface of the newly emerging leaves is deep mauve-purple in color.
2. 'Silver Lady' exhibits leaves that are variegated with olive gray-green centers and thin creamy white margins.

'Silver Lady' can be most closely compared to 'Orphan Annie', the parent plant. 'Orphan Annie' differs from 'Silver Lady' in having leaves that are lighter green in color, and in having leaf margins that are wider, more cream colored, and that occasionally extend into the leaf centers. 'Silver Lady' can also be compared to 'Lady Ann' (not patented). 'Lady Ann' has wider leaf margins that extends into the leaf centers and 'Lady Ann' also develops into a larger sized plant.

BRIEF DESCRIPTION OF THE DRAWING

The accompanying colored photographs illustrate the overall appearance and distinct characteristics of the new *Hebe.*

The photographs were taken of a plant approximately twelve months in age as grown outdoors in a 18 cm container in Auckland, New Zealand.

Figure 1:
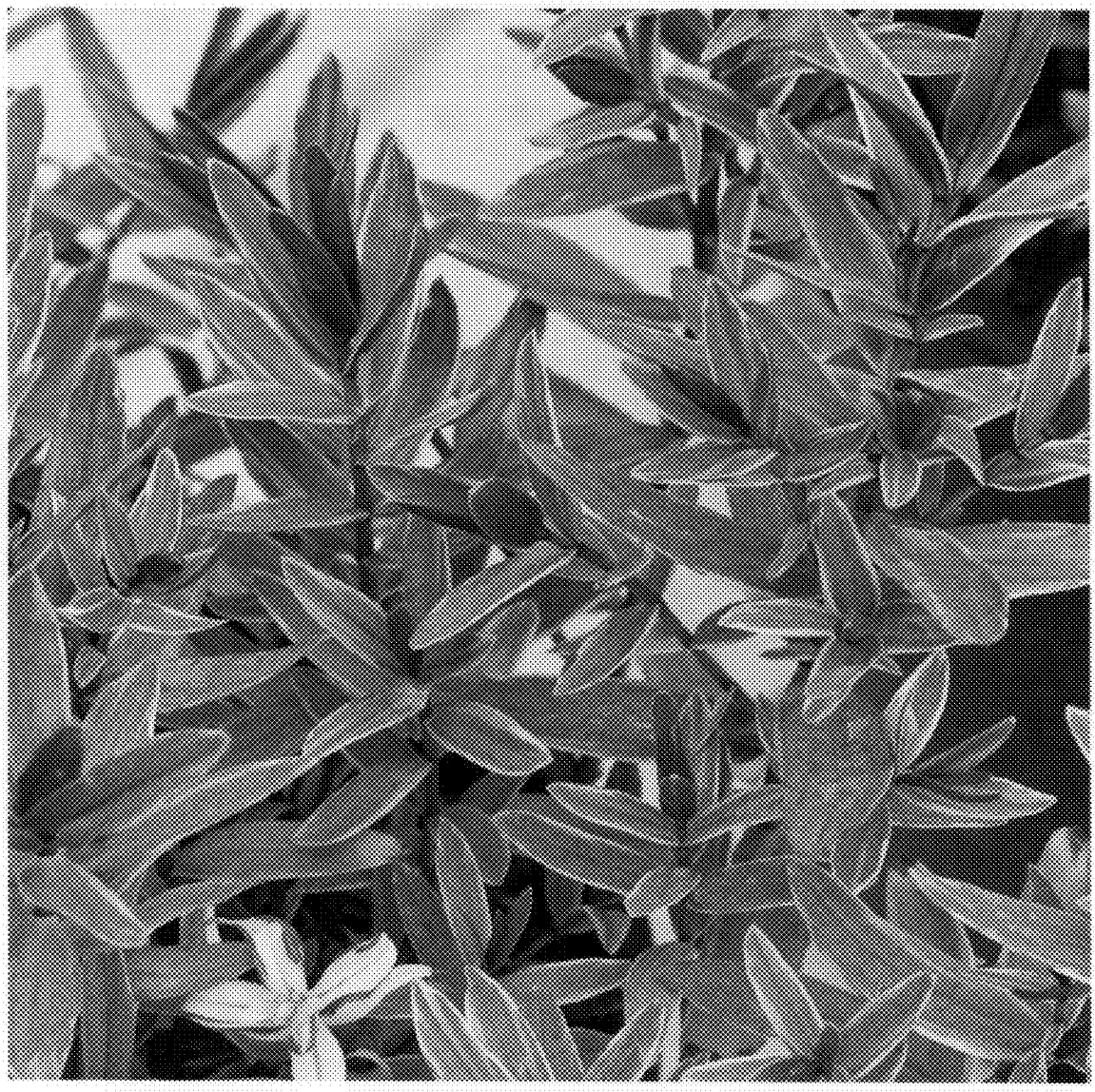
Figure 2:
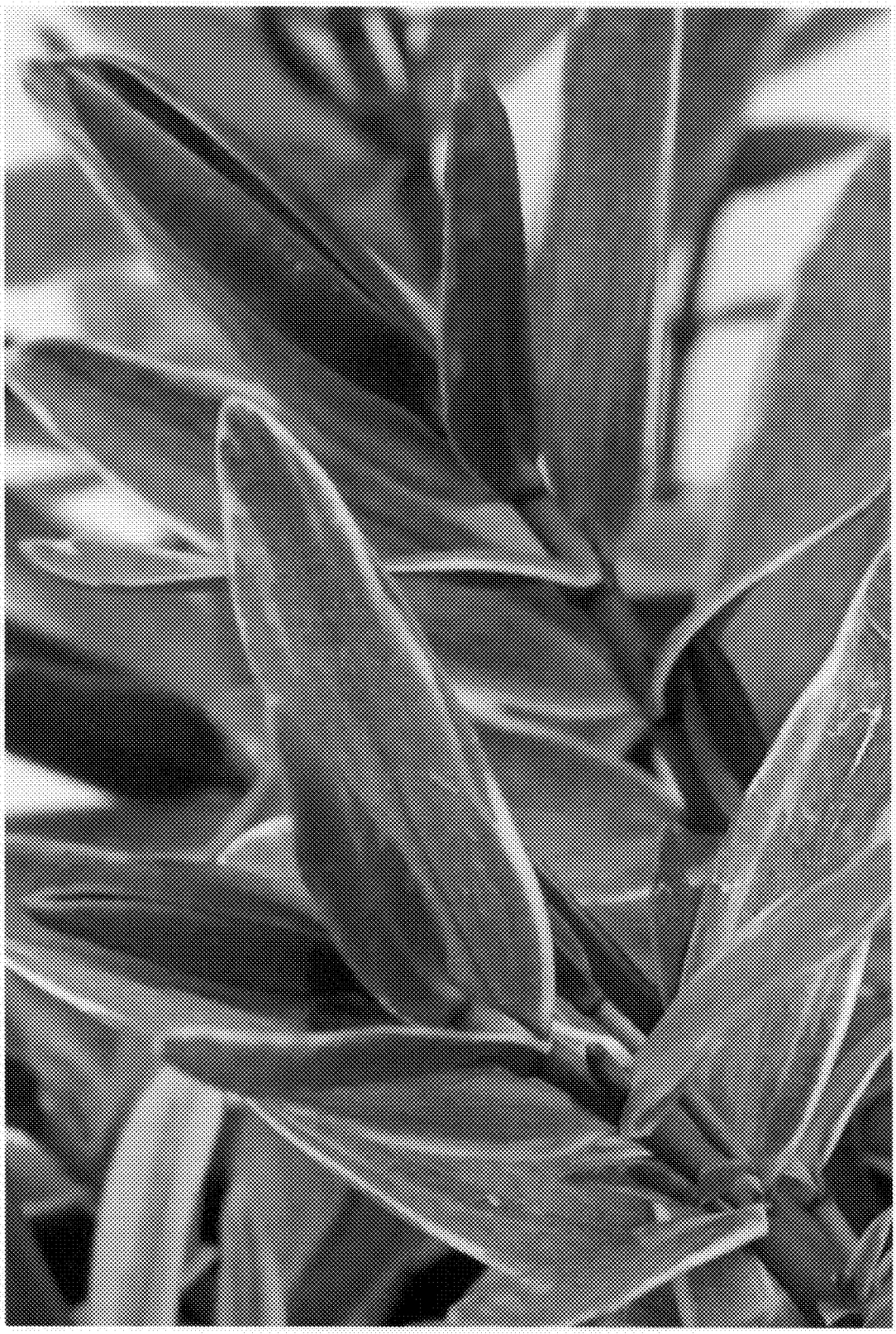

The photograph in FIG. 1 provides a side view of 'Silver Lady' and the photograph in FIG. 2 provides a close-up view of the spring foliage of 'Silver Lady'.

The colors in the photographs may differ slightly from the color values cited in the detailed botanical description, which accurately describe the colors of the new *Hebe.*

DETAILED BOTANICAL DESCRIPTION OF THE PLANT

The following is a detailed description of twelve month-old plants of the new cultivar as grown outdoors in 18 cm containers in Auckland, New Zealand. Plants were grown under average day temperatures of 18° to 24° C. and average night temperatures of 4° to 10° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General plant characteristics:

*Plant type.*—Perennial shrub.

*Plant habit.*—Upright, branching and spreading.

*Flowering period.*—For 12 weeks during late summer in New Zealand.

*Height and spread.*—Reaches about 40 to 70 cm in height and 40 to 50 cm in width in a 18 cm container.

*Hardiness.*—Tolerates temperatures at least from −2° C. to 35° C. and is cold hardy to at least U.S.D.A. Zone 7.

*Disease resistance.*—No particular resistance to diseases has been observed.

*Root description.*—Fibrous and fine, about 1 to 3 mm in diameter, 176D in color.

Propagation and growth:

*Growth rate.*—Vigorous.

*Propagation.*—Terminal stem cuttings.

*Root initiation.*—Roots appear in about 8 days at 20° C. under mist propagation in greenhouse conditions using natural light.

*Root development.*—About 7 weeks of root development before transferring to a 5 cm liner and 12 weeks to fully develop in a 5 cm container having the top growth trimmed once during this period.

Stem description:

*Stem size.*—Lateral branches are an average of 20 to 40 cm in length and 4 to 6 mm in width.

*Stem shape.*—Round.

*Stem color.*—147C.

*Stem surface.*—Glossy.

*Internode length.*—Average of 7 mm.

*Branching habit.*—Freely branched from base, average of 7 lateral branches.

*Branching aspect.*—Mostly upright.

Foliage description:

*Leaf shape.*—Oblong.

*Leaf division.*—Simple.

*Leaf base.*—Broadly cuneate to rounded.

*Leaf apex.*—Broadly acute.

*Leaf venation.*—Pinnate, only mid rib is conspicuous.

*Leaf margins.*—Entire.

*Leaf attachment.*—Sessile.

*Leaf arrangement.*—Opposite.

*Leaf surface.*—Glabrous.

*Leaf color.*—Upper surface immature foliage; centers 189A, margins 157D, lower surface immature foliage; centers N77A , margins N77B, mature foliage upper surface; centers 189A, margins 157D, mature lower surface foliage; centers 191A, margins 157D.

*Leaf number.*—Average of 20 to 30 (10 to 15 pairs) per lateral branch.

*Leaf size.*—Average of 4 to 5 cm in length and 9 to 12 mm in width.

*Leaf aspect.*—Held nearly horizontal to lateral branch when fully mature.

*Leaf fragrance.*—None.

Flower description:

*Inflorescence type.*—Racemes of campanulate flowers, arranged at terminus and in opposite pairs at nodes.

*Inflorescence size.*—Average of 4 to 5 cm in length (excluding peduncle) and 1.5 to 2 cm in width.

*Flower shape.*—Campanulate.

*Flower fragrance.*—None detected.

*Flower quantity.*—Average of 50 to 60 per raceme, average of 2 to 4 racemes per lateral stem, 10 to 12 racemes per plant in a 18 cm container.

*Flower arrangement.*—Packed tightly in a whorl on peduncle with flowers opening from the base towards the apex.

*Flower aspect.*—Slightly drooping.

*Flower lastingness of inflorescence.*—Flowers last about 4 to 6 weeks, 20 to 30% of flowers of raceme are open at one time, flowers are persistent.

*Flower size.*—Average of 7 mm in depth and 6 mm in diameter.

*Peduncles.*—Average of 1 to 2 cm in length and 1 mm in diameter, 146C in color, surface is covered with very short hairs, round in shape, held at about a 30° angle to stem.

*Pedicels.*—Average of 2 mm in length and <1 mm in width, held at about a 50° to 60° angle to peduncle, 146C in color, surface is glabrous.

*Flower buds.*—Narrowly elliptical in shape, average of 1 to 2 mm in length and 0.5 to 1 mm in diameter, 70A in color.

*Calyx.*—Rotate, average of 1.5 mm in length and 2 mm in width.

*Sepals.*—3, lanceolate in shape, margin is entire, apex is acute, base tapers into pedicel, color of upper and lower surface is 138C, average of 1.5 mm in length and 1 mm in width.

*Petals.*—3 to 4, about 3 to 4 mm in length and 1 to 2 mm in width, oblanceolate in shape, entire margins, apex obtuse, upper and lower surface is glabrous, color of upper surface when opening; 70B with throat 69B, color of lower surface when opening; 70C, color of upper surface when fully open; 70B with throat 69B, color of lower surface when fully open; 70C, color of both surfaces after fading; 69D.

Reproductive organs:

*Gynoecium.*—1 Pistil, 8 to 9 mm in length, stigma is clavate in shape and about 72A in color, style is about 6 to 7 mm in length and 72B in color, ovary is 148C in color.

*Androcoecium.*—2 stamens, anthers are elliptic in shape and dorsifixed, about 1 mm in length and 72A in color, pollen is minimal in quantity.

*Fruit and seed.*—Seed production has not been observed.

It is claimed:

1. A new and distinct cultivar of *Hebe* plant named 'Silver Lady' as herein illustrated and described.

* * * * *